(12) United States Patent
Field

(10) Patent No.: US 8,858,509 B2
(45) Date of Patent: Oct. 14, 2014

(54) NEEDLE BASED HELICAL COIL SAFETY DEVICE

(75) Inventor: Frederic P. Field, San Diego, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 196 days.

(21) Appl. No.: 13/101,585

(22) Filed: May 5, 2011

(65) Prior Publication Data

US 2011/0276029 A1 Nov. 10, 2011

Related U.S. Application Data

(60) Provisional application No. 61/331,757, filed on May 5, 2010.

(51) Int. Cl.
*A61M 5/32* (2006.01)
(52) U.S. Cl.
CPC ......... *A61M 5/326* (2013.01); *A61M 2005/325* (2013.01); *A61M 5/3275* (2013.01); *A61M 2005/3249* (2013.01); *A61M 5/3257* (2013.01)
USPC ........................................................ 604/198
(58) Field of Classification Search
USPC ................................................. 604/198, 506
See application file for complete search history.

(56) References Cited

U.S. PATENT DOCUMENTS 4,725,267 A * 2/1988 Vaillancourt ................. 604/192
5,256,152 A * 10/1993 Marks ........................... 604/198
5,364,370 A 11/1994 Szerlip et al.
5,700,247 A 12/1997 Grimard et al.
6,261,264 B1 7/2001 Tamaro
6,296,625 B1 10/2001 Vetter et al.
2004/0199112 A1 10/2004 Dalton
2009/0036839 A1 2/2009 Phalen
2009/0270814 A1 10/2009 Masi et al.

FOREIGN PATENT DOCUMENTS

| WO | WO 89/10767 | 11/1989 |
| WO | WO 94/01152 | 1/1994 |
| WO | WO 02/070055 A1 | 9/2002 |
| WO | WO 2008/092958 | 8/2008 |

OTHER PUBLICATIONS

WO, International Search Report for PCT/US2011/035066, Authorized Officer: Blaine R. Copenheaver, Aug. 18, 2011.
EP, 1177834.6 Supplementary Search Report, Oct. 14, 2013.

* cited by examiner

*Primary Examiner* — Kevin C Sirmons
*Assistant Examiner* — Deanna K Hall
(74) *Attorney, Agent, or Firm* — One LLP

(57) ABSTRACT

The present disclosure describes anti-needle stick safety mechanism that is passively activated during the normal course of giving an injection. In one embodiment, the device includes a spring member coupled at a proximal end to a needle member and at a distal end to a needle cover. The passive activation of the device is triggered when the needle is inserted to a minimum depth into the patient's tissue to unleash the force of a compressed spring to urge a needle cover towards the distal end of the needle. As the needle is withdrawn from the tissue, the needle cover advances to the end of the needle and as it partially clears the end of the needle, it adopts an orientation that prevents the needle tip from re-emerging from the needle cover.

24 Claims, 14 Drawing Sheets

NEEDLE BASED HELICAL COIL SAFETY DEVICE

CROSS-RELATIONSHIP TO PENDING APPLICATIONS

This application claims priority to provisional application Ser. No. 61/331,757 filed May 5, 2010, which is incorporated herein by reference.

FIELD

The embodiments provided herein relate generally to syringe systems for administering therapeutic agents to patients. More specifically, the embodiments relate to a needle stick safety device.

BACKGROUND

Injecting medicine directly into tissue through a hollow bore needle remains a preferred method of administration many drugs. Once a needle has been used to give an injection, contact with the needle can transmit tissue borne diseases to health care workers, patients, and anyone else who could come in contact with the used injection device. If the subsequent contact also involves a puncture of the skin, disease transmission becomes much more likely.

Accordingly, an improved safety device mountable on a needle device that facilitates prevention of needle stick injuries by way of a mechanism that covers and isolates the needle after injection is desirable.

SUMMARY

The embodiments presented herein are directed to preventing needle stick injuries by way of a mechanism that covers and isolates the needle after injection. The subject anti-needle stick safety mechanism is passively activated during the normal course of giving an injection. In one embodiment, the device includes a spring member coupled at a proximal end to a needle member and at a distal end to a needle cover. The spring member is expandable from a compressed state to a natural expanded state to cover the needle and orient the needle cover to isolate the needle tip.

The passive activation of the device is triggered when the needle is inserted to a minimum depth into the patient's tissue. When this has occurred, the force of a compressed spring is unleashed urging a needle cover towards the distal end of the needle. As the needle is withdrawn from the tissue, the needle cover advances to the end of the needle and as it partially clears the end of the needle, it adopts an orientation that prevents the needle tip from re-emerging from the needle cover.

Other systems, methods, features and advantages of the example embodiments will be or will become apparent to one with skill in the art upon examination of the following figures and detailed description.

DESCRIPTION OF THE DRAWINGS

The details of the example embodiments, including structure and operation, may be gleaned in part by study of the accompanying Figures, in which like reference numerals refer to like parts. The components in the Figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

It should be noted that elements of similar structures or functions are generally represented by like reference numerals for illustrative purpose throughout the figures. It should also be noted that the figures are only intended to facilitate the description of the preferred embodiments.

DETAILED DESCRIPTION

Each of the additional features and teachings disclosed below can be utilized separately or in conjunction with other features and teachings to produce systems and methods to facilitate needle stick prevention. Representative examples of the present invention, which utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

Turning to the figures, the embodiments presented herein are directed to preventing needle stick injuries by way of a mechanism that covers and isolates the needle after injection. The subject anti-needle stick safety mechanism is passively activated during the normal course of giving an injection so that the user does not need to learn or remember any extra operational steps. This contrasts with manually activated devices, which require extra actions such as manually extending a shield over the needle after the injection is given. Although the injections described herein concern those done with a Luer needle, it is understood that the needle could also be of the staked variety, where the needle is pre-attached to the syringe or whatever injection device is being used. It could also be miniaturized to fit underneath the needle shield used with staked needles.

Figure 1:
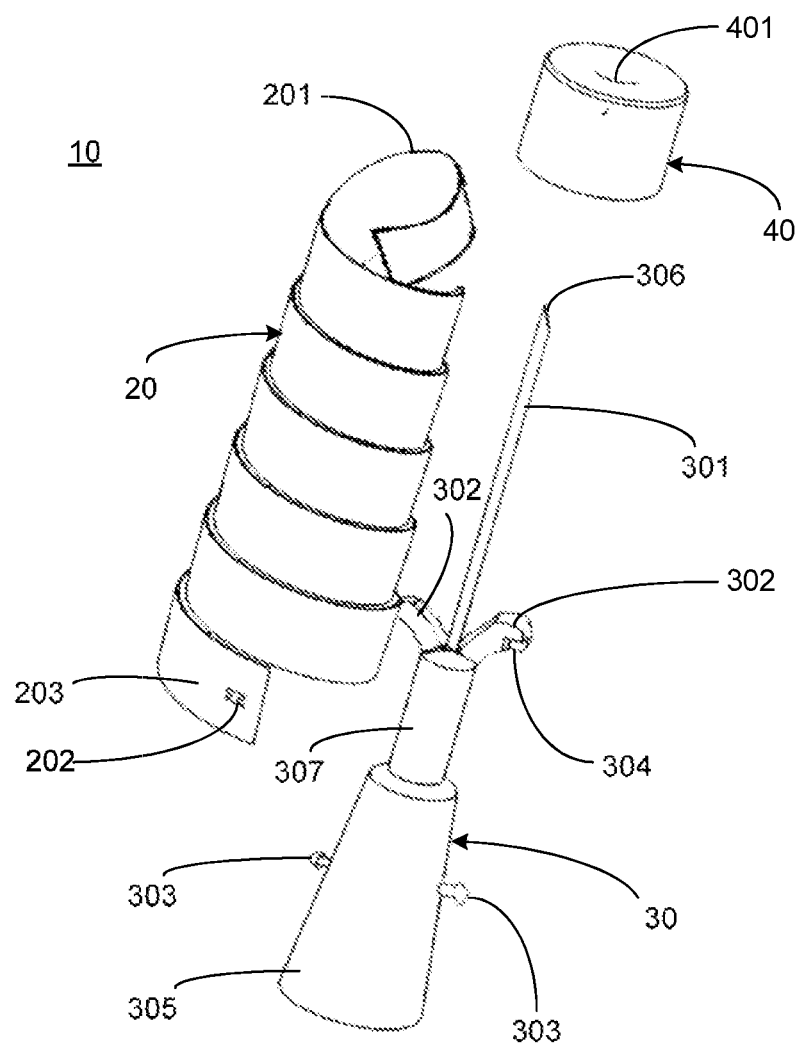
FIG. 1 shows an exploded isometric view of an embodiment of an anti-needle stick safety device.
Figure 2:
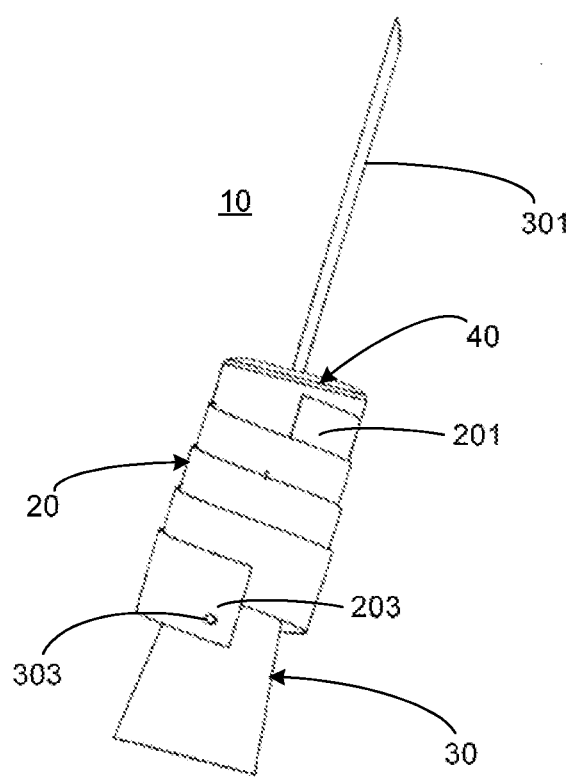
FIG. 2 shows an assembled isometric view of the anti-needle stick safety device in a pre-injection or retracted state.

The subject anti-needle stick safety device 10 is depicted in an exploded orientation in FIG. 1 and in an assembled orientation in FIG. 2. The passive activation of the device 10 is triggered when the needle 301 is inserted to a minimum depth into a patient's tissue. When this has occurred, the force of a compressed spring 20 is unleashed urging a needle cover 40 towards the distal end of the needle 301. As the needle 301 is withdrawn from the tissue, the needle cover 40 advances to the end of the needle 301 and as it partially clears the end of the needle 301, it adopts an orientation that prevents the needle tip from re-emerging from the needle cover 40. The details of this mechanism will be described below.

Figure 7:
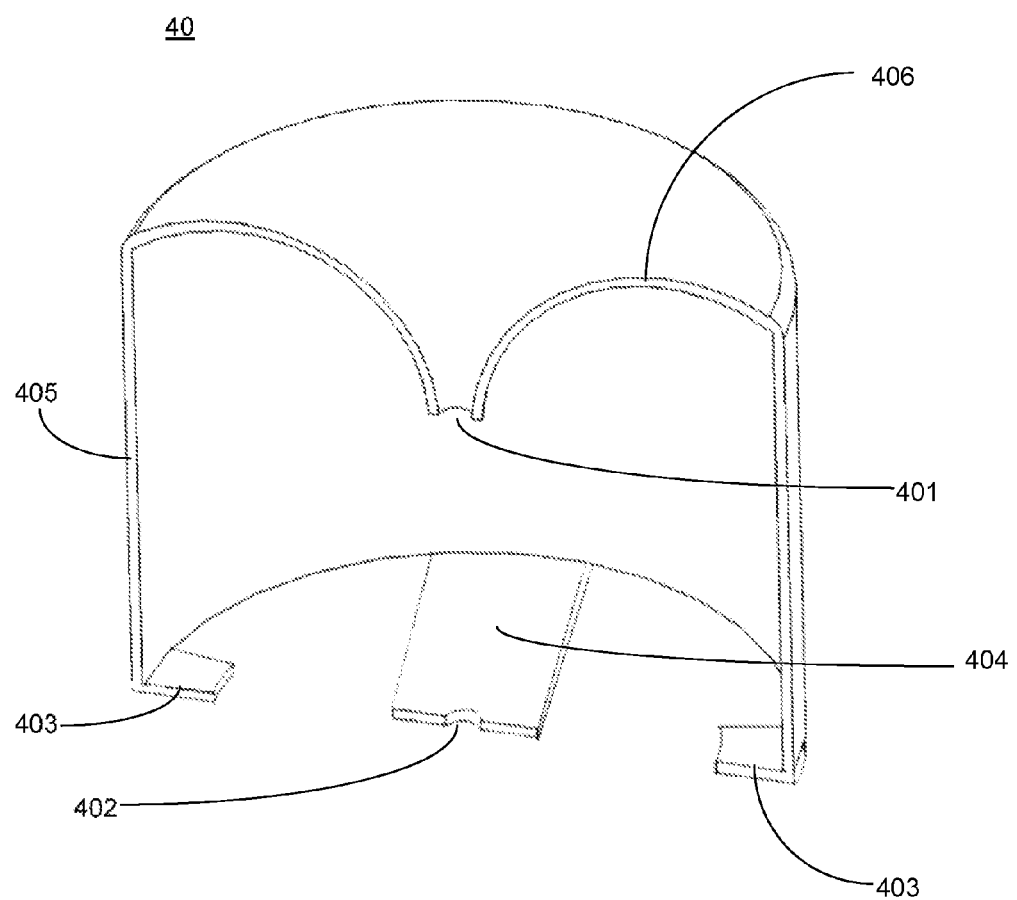
FIG. 7 shows an isometric sectional view of an embodiment of a needle tip cover.

In one embodiment as depicted in FIG. 1, the device comprises three main components comprising a Luer needle 30, a spring member 20, and a needle cover 40. Referring to FIGS. 1 and 7, the shaft 301 of the Luer needle 30 is a standard type of hollow bore needle used for giving injection of medications or the removal of body fluids from patients or animals. The distal end 306 of the shaft has a beveled surface suitable for penetration into tissue. The Luer needle 30 has at its proximal end a Luer fitting 305, which is a standard medical industry fluid transfer attachment for syringes, valves, etc. A pair of mounting pins 303 used to mount the spring member 20 extend in opposite directions from the Luer fitting 305. A pair of latch arms 302 having recesses 304 used to retain the needle tip cover 40 in a pre-injection state extend from a needle shaft mounting base 307.

As shown, the spring member 20 is preferably a flat helical spiral coil spring. The spring member 20 is preferably formed from a thin stainless steel OR nitinol metal sheet, preferably about 0.003 inches thick, having a high tensile strength so that it can sustain high strains without permanently deforming. A helical spiral coil spring member 20 is made with a thin portion of steel stamped into the shape shown in FIG. 1. The central part is wound tightly such that its natural configuration is an elongated helix with wide walls, which form a continuous covering protecting the needle 301 inside from potentially contacting and contaminating health care providers, etc.

The needle tip cover 40 can be attached to the distal coils 201 of the helical spiral coil spring 20 using a press fit arrangement, mounting pins as shown on the Luer needle 30, glue, or a spot weld operation. It is also possible that needle tip cover 40 could be integrally formed from the geometry of the distal coils 201 of the helical spiral coil spring 20 by way of a progressive die manufacturing process to form a cup shape at the distal end of the coil spring 20.

As depicted, the proximal coils 203 include one or more mounting holes 202 formed therein to engage the mounting pins 303 on the Luer needle 30. Preferably the mounting pins 303 press fit into the mounting holes 202 to couple the helical spiral coil spring 20 to the Luer needle 30.

FIG. 2 depicts the device 10 in the assembled configuration and ready to be attached to a syringe in preparation for giving an injection. As depicted, the needle tip cover 40 is in a first, retracted position mounted along the needle shaft 301 of the Luer needle 30 and the helical spiral coil spring 20 is compressed.

Figure 3:
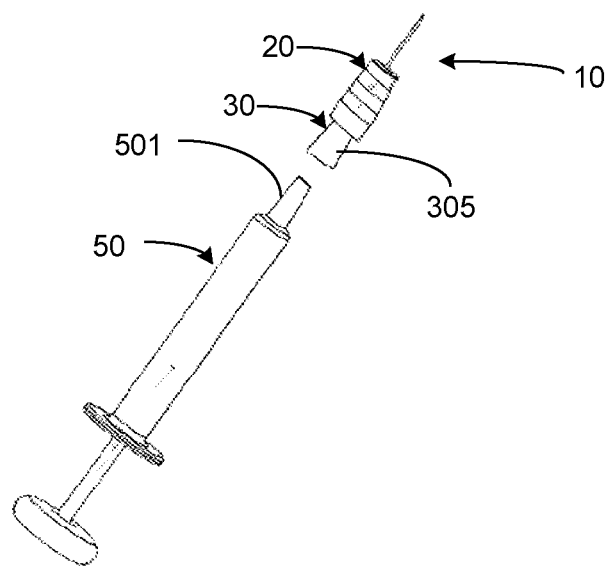
FIG. 3 shows an exploded isometric view of the anti-needle stick safety device ready for assembly with a syringe with a Luer fitting.
Figure 4:
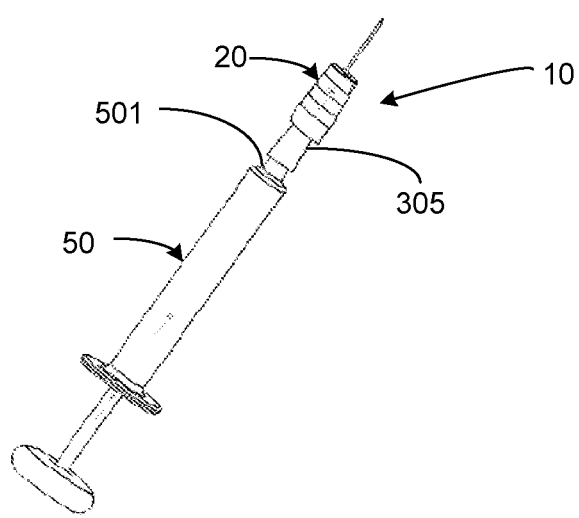
FIG. 4 shows an assembled isometric view of the anti-needle stick safety device assemble with a syringe with a Luer fitting in a pre-injection or retracted state.

A syringe 50 with a Luer fitting 501 is depicted in FIG. 3. Prior to use in an injection, the Luer fitting 305 of the Luer needle 30 of the anti-needle stick safety device 10 is coupled to the Luer fitting 501 of the syringe 50, as shown in FIG. 4.

Figure 5:
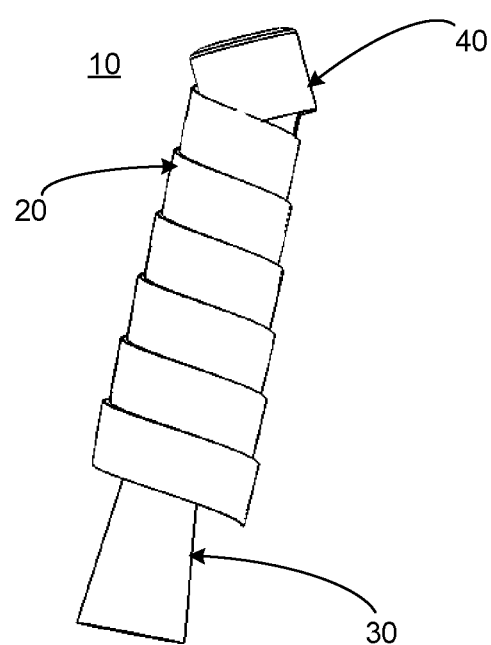
FIG. 5 shows an assembled isometric view of the anti-needle stick safety device in a post-injection safety configuration or extended (needle shielded) state.
Figure 6:
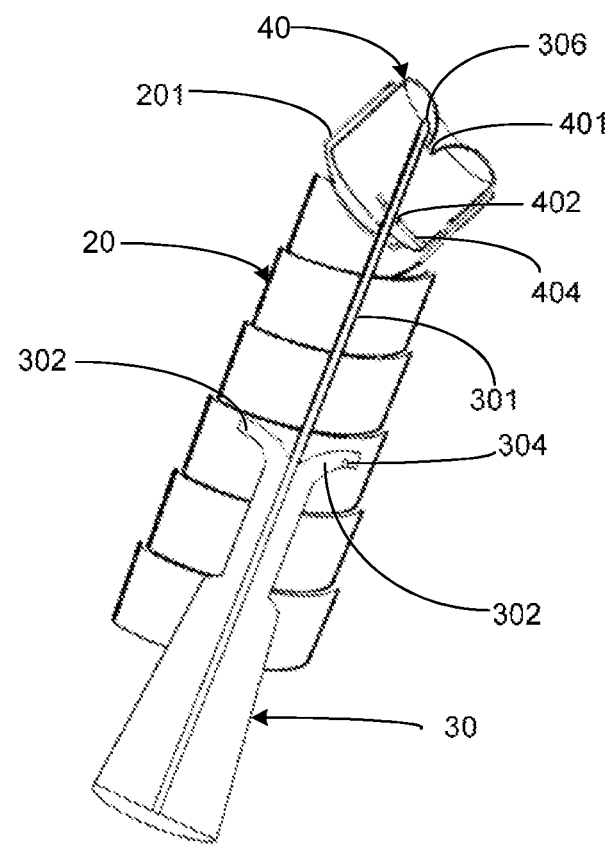
FIG. 6 shows a sectional view of the anti-needle stick safety device in a post-injection safety configuration or extended (needle shielded) state.

As depicted in FIGS. 1, 5 and 6, the distal coils 201 of helical spiral coil spring 20 are oriented at an angle to the helical spiral coil spring 20 axis and the shaft of needle 301. The needle tip cover 40 is attached to the distal coils 201. The distal coils 201 allow the needle tip cover 40 to elastically align to the shaft of needle 301 when the helical spiral coil spring 20 and needle tip cover 40 are fully assembled as shown in FIG. 2. When the needle tip cover 40 is positioned beyond the tip 306 of needle 301 as shown in FIGS. 5 and 6, the elastic force of the distal coils 201 urge the needle tip cover 40 to become angled with respect to the shaft of the needle 301 in a safety configuration.

As depicted in FIGS. 5 and 6, when the anti-needle stick safety device 10 is triggered as discussed below, the helical spiral coil spring 20 is extended to its natural configuration forcing the needle tip cover 40 to partially clear the distal tip 306 of needle 301 and allowing it to cover and isolate the tip 306 of needle 301. The needle tip cover 40 is at an angle to the shaft of needle 301 thus jamming the needle shaft 301 against a locking hole 402 to secure it to prevent relative motion of the needle tip cover 40 with respect to the needle tip 306.

Figure 8:
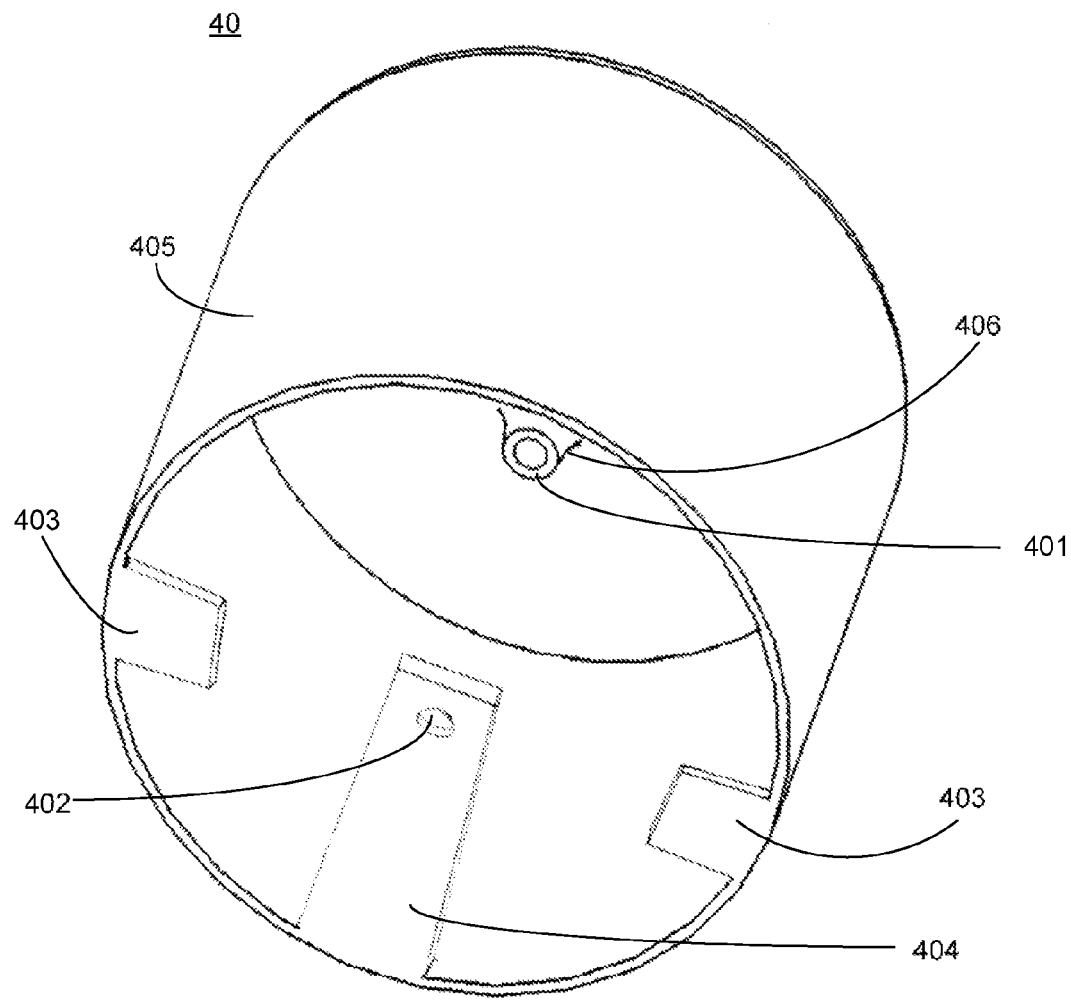
FIG. 8 shows an isometric view of the needle tip cover from the proximal end of the needle tip cover.
Figure 9:
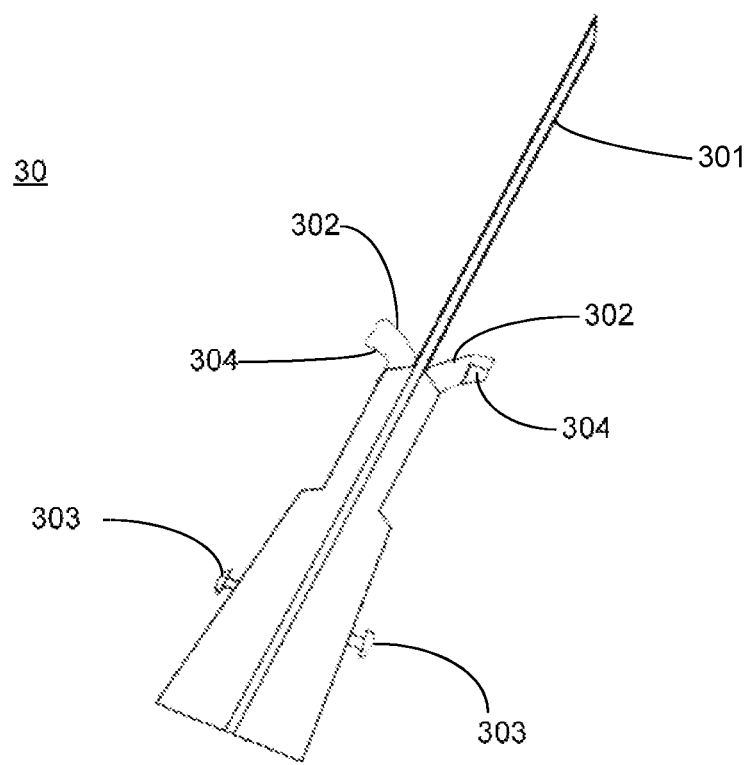
FIG. 9 shows a sectional view of an embodiment of a Luer needle.

The details of the needle tip cover 40 are shown in FIGS. 7 and 8. As depicted, the needle tip cover 40 is generally cup shaped with a cylindrical side wall or body 405 and an inwardly chamfered or concave distal surface 406 (in the proximal direction) with a distal hole 401 at the center of the distal surface 406. The shape of the distal hole 401 and surrounding surface 406 allow passage of the needle shaft 301 and the collection of any body fluids at a recessed point to avoid possible contact with health care providers during withdraw of the needle 301. The concave surface 406 is projected to the interior of the needle tip cover 40 as can be seen in the sectional view of FIG. 7. As the tip 306 of the needle 301 moves proximally with respect to the needle tip cover 40 and as the needle tip 306 clears the proximal edge of the distal hole 401, the needle tip cover 40 can become angled with respect to the axis of the needle shaft 301 allowing the tip 306 of the needle 301 to be directed away from the distal hole 401.

The locking hole 402, which is formed in a locking arm 404, is in substantial axial alignment with the distal hole 401. As the needle tip cover 40 becomes angled with respect to the axis of the needle shaft 301, the locking hole 402 jams against the needle shaft 301 and secures the needle tip cover 40 relative to the needle tip 306.

Figure 10:
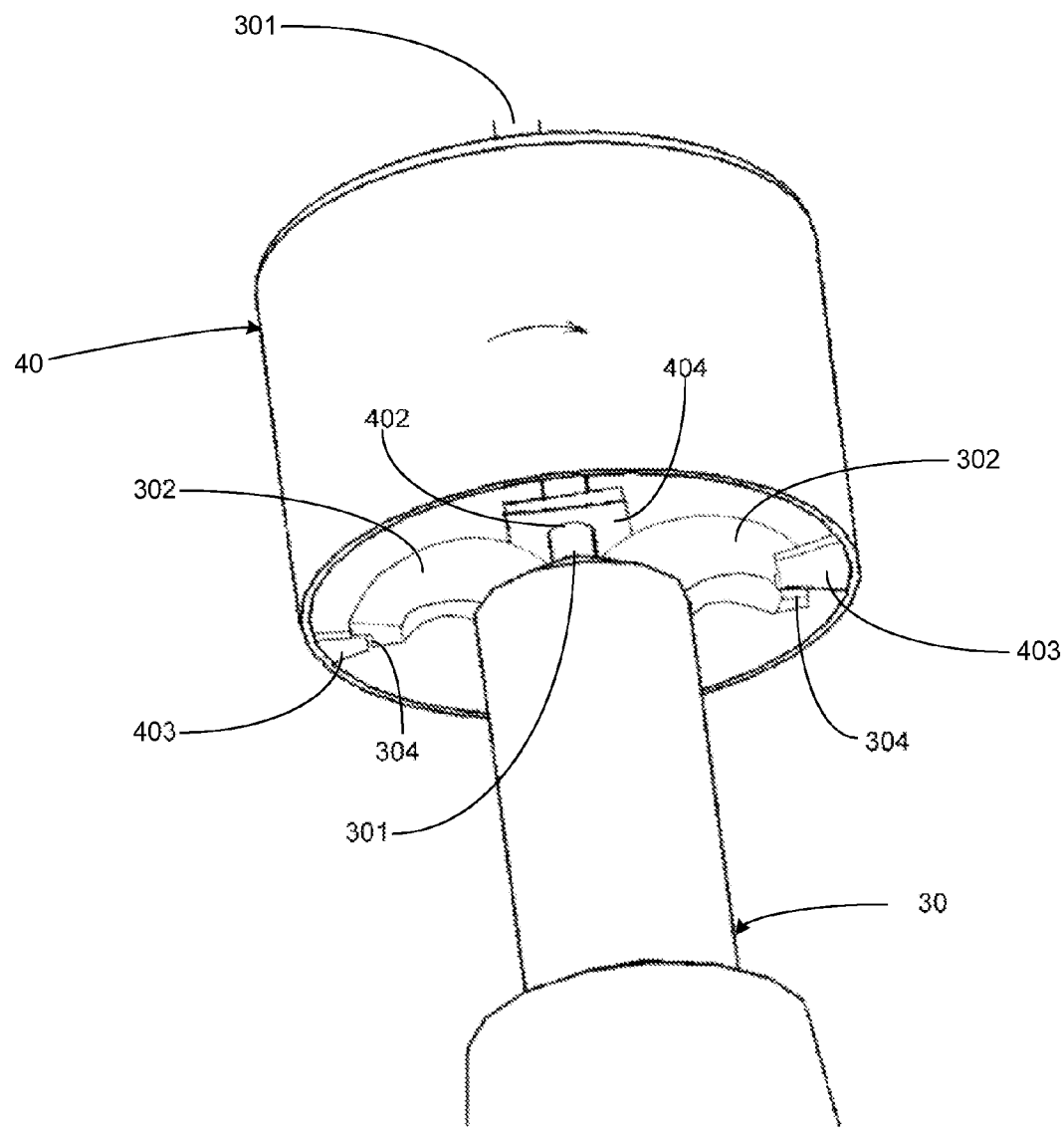
FIG. 10 shows an orthogonal view from a proximal end of the Luer needle and needle tip cover in an assembled configuration ready to trigger the safety mechanism after injection of a medication into tissue of a patient. The helical coil spring has been removed from the Figure for clarity.
Figure 11:
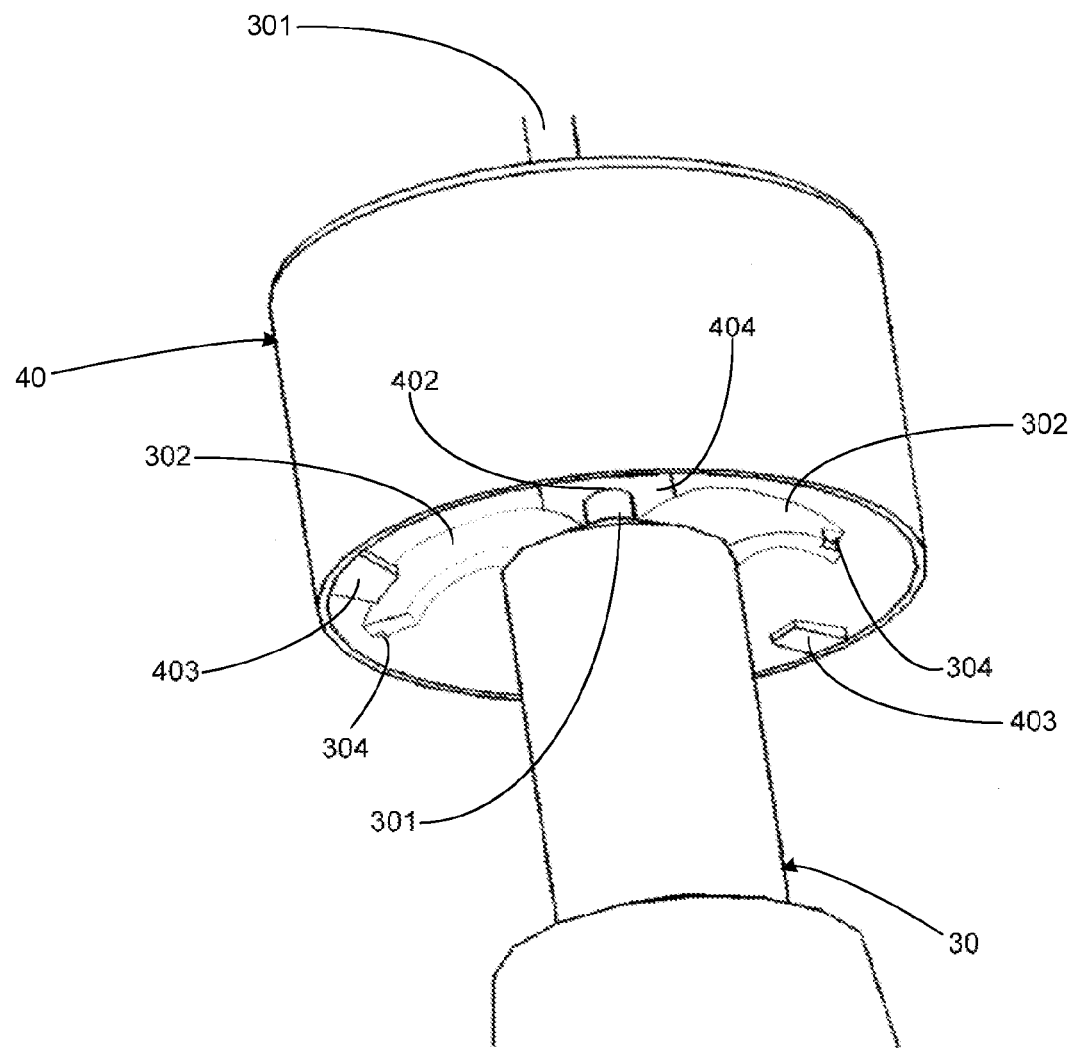
FIG. 11 shows an orthogonal view from a proximal end of the Luer needle and needle tip cover in an assembled configuration just after injection of a medication into tissue of a patient and the safety mechanism has been triggered. The helical coil spring has been removed from the Figure for clarity.
Figure 12:
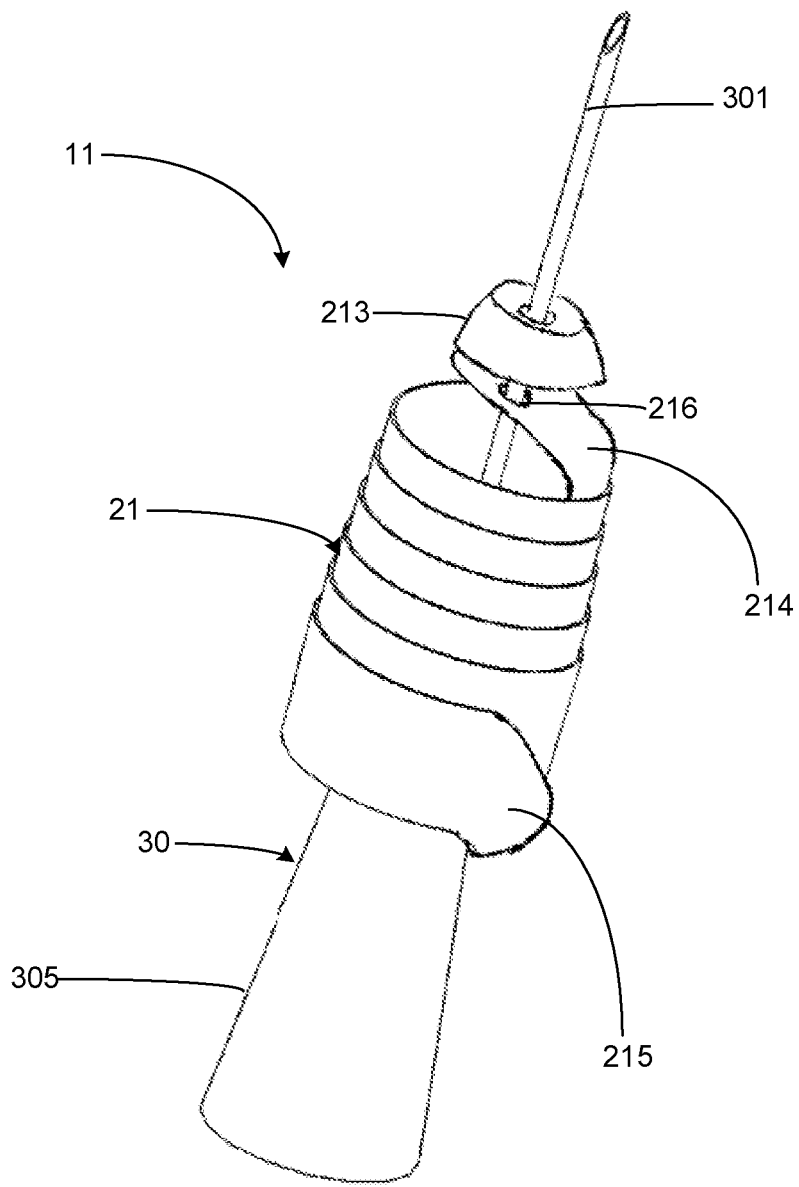
FIG. 12 shows an orthogonal view of an embodiment of an assembled one-piece anti-needle stick safety device in a pre-injection or retracted state.

The needle tip cover 40 has one or more latches 403 that engage with one or more recesses 304 in one or more needle cover latch arms 302 shown in FIGS. 1, and 6 through 11. The latches 403 resist distal movement of the needle tip cover 40 in response to the distally directed force of the helical spiral coil spring 20 when the latches 403 are engaged with the latch recesses 304 as shown in FIG. 10. The lateral surfaces of the latches 403 engage with corresponding lateral surfaces of the latch recesses 304 of the latch arms 302 to prevent clockwise rotation of the needle tip cover 40 (clockwise as viewed from the proximal end of the device looking in a distal direction). During assembly, the needle tip cover 40 is pushed down the shaft of the needle 301 and is given a slight counter clockwise (as viewed from the proximal end) rotational twist against the rotational elasticity of the helical spiral coil spring 20 before the distal surfaces of the latches 403 are allowed to come to rest against the proximal edges of the latch recesses 304. The helical spiral coil spring 20 distally directed axial force is held in check by the mating distal surfaces of the latches 403 and proximal surfaces of latch recesses 304. The stored rotational energy of the helical spiral coil spring 20 as a consequence of the twist imparted during assembly maintains a clockwise directed rotational torque to the needle tip cover 40 (shown by the arrow in FIG. 8) urging the latches 403 into the latch recesses 304. More importantly, when the needle tip cover 40 is moved proximally during contact with injection site tissue, the needle tip cover 40 will rotate causing the latches 403 to unseat and move away from the latch recesses 304. At this point the safety mechanism 10 has been triggered. As the needle tip cover 40 begins to move distally as the needle 301 is withdrawn from the patient, the latches 403 clear the latch recesses 304 allowing the needle tip cover 40 to move to the distal end of the needle 301 in response to the force stored in the helical spiral coil spring 20.

The entire safety device 10 would normally be packaged in a sterile enclosure, which has not been shown for clarity. A typical sequence of steps for using the device 10 would be for a health care provider or self administrating patient to remove the device 10 from the sterile enclosure and attach the device 10 to the Luer fitting 501 of the syringe 50 (FIGS. 3 and 4) or other device containing the prescribed medication. After locating and preparing the injection site, the needle 301 would be pushed into the tissue. The initial position of needle tip cover 40 on the shaft of the needle 301 is such that as the needle 301 is advanced into the tissue, the tissue pushes against the needle tip cover 40, which disengages the needle tip cover latches 403 from the needle latch recesses 304 and allows the helical spiral coil spring 20 to urge the needle tip cover 40 towards the tip 306 of the needle 301. The force of the spring 20 is small enough to not interfere with the user positioning the needle 301 to the appropriate tissue depth. After the medication has been dispensed (or body fluid withdrawn), the user pulls the device 10 away from the tissue and under the force of the helical spiral coil spring 20, the needle tip cover 40 continues to rest against the tissue as the needle 301 is withdrawn. With further withdraw of the needle 301, the needle tip 306 emerges from the tissue and eventually the needle tip cover 40 is pushed beyond the tip 306 of the needle 301 so that the needle tip 306 clears the confines of the needle tip cover distal hole 401 (FIG. 6). At this point, the elastic force of the distal coils 201 angles the needle tip cover 40 with respect to the needle shaft 301 and the needle tip cover locking hole 402 engages the shaft 301 of the needle. Consequently, the tip 306 of the needle 301 is pointed away from the needle cover distal hole 401 and the locking hole 402 has engaged the needle shaft 301 with the edges of the proximal and distal surfaces of the locking hole 402.

The needle tip cover locking hole 402 is preferably made of a material that is harder than the needle shaft 301 and is formed with crisp edges and a diameter such that when the tip cover 40 is put at an angle after clearing the needle tip 306, the locking hole 402 is able to bite into the needle shaft 301 with enough force to prevent movement of the tip cover 40 relative to the needle shaft 301. The main purpose of the locking hole-shaft 402-301 engagement is to prevent the needle tip cover 40 from being pushed distally off the needle tip 306 since proximally directed forces, which would be typical during a needle stick accident, would tend to push the tip 306 of the needle 301 into the distal exterior corner of the needle tip cover 40 where it will be stably contained. The needle tip cover 40 is preferably made of a material that is hard enough to prevent the needle tip 306 from penetrating its wall.

Referring to FIGS. 12-15, an alternative embodiment comprising a one-piece anti-needle stick safety device 11 is shown. As depicted, the one-piece anti-needle stick safety device 11 comprises an integral needle tip cover 213 that could be formed from the distal material of the helical spiral coil spring 21 as by a progressive die manufacturing method. The proximal attachment of the helical spiral coil spring 21 to the Luer needle 30 is shown with an inwardly bent proximal coil 215 with a proximal locking hole 217. As with the other applications of a locking hole described herein, the proximal locking hole 217 would be sized so as to grasp the needle shaft 301 when the proximal locking hole 217 was angled from the perpendicular with respect to the axis of the needle 301. The inwardly bent proximal coil 215 would maintain an angle greater or less than perpendicular to the needle shaft 301 so that the proximal locking hole 217 secured the proximal end of the helical spiral coil spring 21 to the needle 301. This attachment, rather than attaching the proximal end of the helical spiral coil spring 21 to the Luer needle 30 as shown in FIG. 2, could be used for placing the entire anti-needle stick safety device 21 underneath a needle shield, which is used to form a seal between the tip of the needle and the proximal area of the needle in order to keep this area sterile after a sterilization procedure such as treatment with ethylene oxide (eto).

Figure 13:
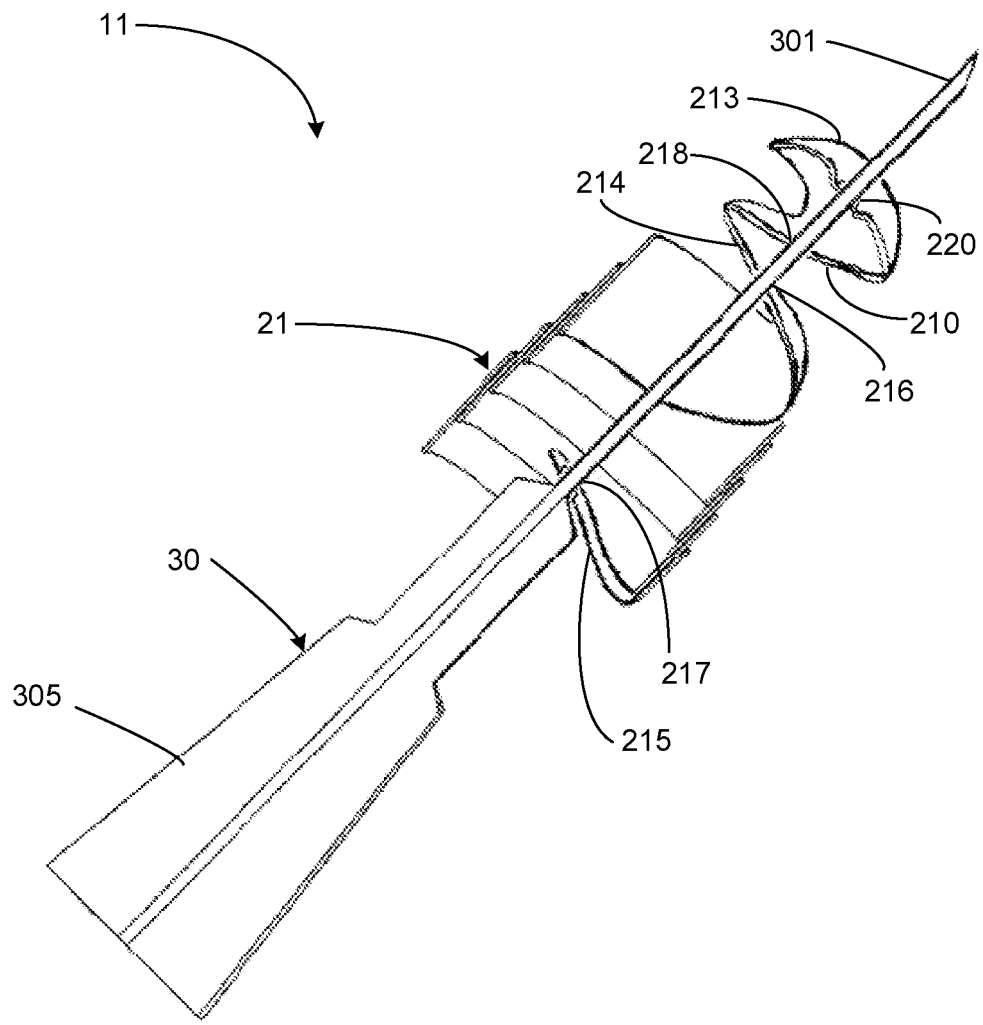
FIG. 13 shows a sectional view of the one-piece anti-needle stick safety device shown in FIG. 12.
Figure 14:
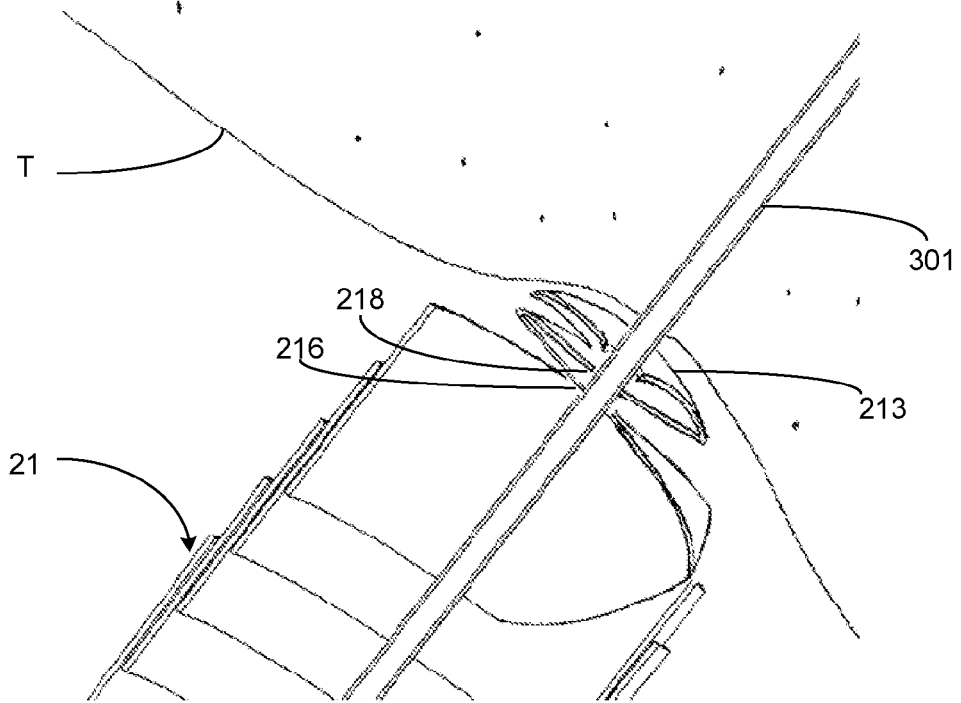
FIG. 14 shows a sectional view of the one-piece anti-needle stick safety device shown in FIG. 12 with the needle embedded in tissue.
Figure 15:
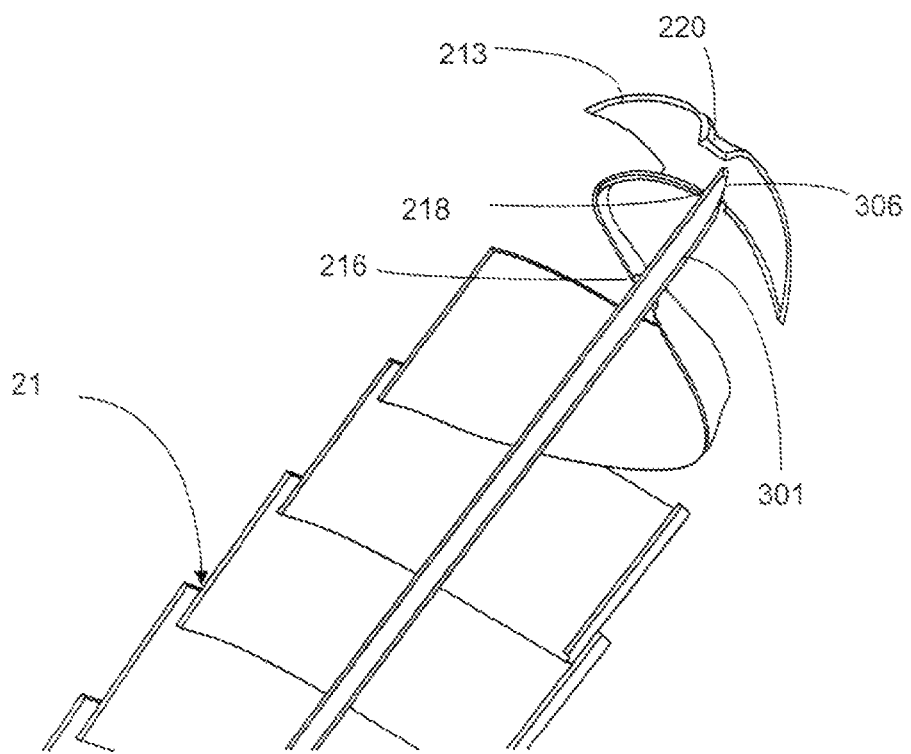
FIG. 15 shows a sectional view of the one-piece anti-needle stick safety device shown in FIG. 12 with the needle withdrawn from the tissue and the device in a needle-stick safety configuration with the integral needle tip cover covering the distal end of the needle.

At the distal end of the helical spiral coil spring 21 is an inwardly bent first distal coil 214 with a first distal locking hole 216. In the assembled configuration, inwardly bent first distal coil 214 holds the first distal locking hole 216 at a non-perpendicular angle to the longitudinal axis of the needle 301. In this orientation, the first distal locking hole 216 holds the position of the integral needle tip cover 213 on the needle 301 against the force of the spring 21 at a position that exposes the needle 301 for insertion into tissue T (FIG. 14). Located distally to the inwardly bent first distal coil 214 with the first distal locking hole 216 is a second bent distal coil 210 inwardly bent at a second direction relative to the inwardly bent first distal coil 214 as shown in FIG. 13. The second bent distal coil 210 includes a second distal locking hole 218. Inwardly bent first distal coil 214 and second bent distal coil 210 have a spring bias between them that attempts to increase the angle between each other and maintain non-perpendicular orientations of their respective locking holes 216 and 218 to further increase the grasp they have on the needle. With this internal spring bias, the integral needle tip cover 213 can be positioned and held for the life of the product at a desired position along the length of the needle 301 with the helical spiral coil spring 21 under compression. With a proximally directed force from the tissue T during needle insertion, directed against the integral needle tip cover 213 (FIG. 14) the spring bias between the inwardly bent first distal coil 214 and second bent distal coil 210 is overcome, reducing the angle between them and causing the locking holes 216 and 218 to have an angle with respect to the axis of the needle 301 close to perpendicular, thereby releasing their grasp on the needle 301 and allowing the integral needle tip cover 213 to slide along the needle shaft. As the needle 301 is withdrawn from the tissue T, the integral needle tip cover 213 slides to the end of the needle 301 (FIG. 15). At this point, the inwardly bent first distal coil 214 has resumed its non-perpendicular orientation with respect to the axis of the needle 301 thereby allowing the first distal locking hole 216 to engage the shaft of the needle 301. The tip 306 of the needle 301 has become positioned proximal to the opening of the integral needle tip cover 213 and as the second distal locking hole 218 clears the tip 306 of the needle 301 (shown partially progressed in FIG. 15), the spring bias of the second bent distal coil 210 displaces the integral needle tip cover 213 so that the needle tip 306 is not aligned to the distal hole 220 and is prevented from re-emerging from the integral needle tip cover 213.

For the sake of visualization, the integral needle tip cover 213 and the distal coils of the helical spiral coil spring 214 and 210 have been shown with gaps between the components, which would be normally minimized to provide for maximum isolation of the contaminated needle from the external environment.

While a typical coil spring made with round wire could provide the elastic force for moving the needle tip cover to the end of the needle, it would potentially allow exposure of biological contaminants on the shaft of the needle to health care workers via the spaces between coils. Furthermore, it is desirable to make the safety device as small as reasonable possible so that storage and hazardous disposal volumes are minimized. Since standard coil springs have solid heights, which are significant compared to their extended lengths, they could necessitate the use of a longer, and therefore, more flimsy, needle than would normally be used. It is desirable, therefore, to have a spring, such as the helical spiral spring herein depicted, that adopts the shortest compressed length for a given amount of elastic travel and that forms a continuous cylindrical structure in the elongated state to prevent the transfer of contaminants from the needle to the health care environment.

While the invention is susceptible to various modifications, and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

What is claimed:

1. A passive safety device for use with a syringe comprising a Luer needle having a Luer connector and a needle shaft extending from the Luer connector, the Luer needle having a first latch member,
a helical spiral coil spring coupled at a proximal end to the Luer connector of the Luer needle, and
a needle cover coupled to the helical spiral coil spring at a distal end and slidably receivable over the needle shaft, the needle cover having a second latch member cooperatable with the first latch member to retain the needle cover in a first refracted position along the needle shaft, wherein when the needle cover is retained in the first retracted position the helical spiral coil spring is biased to urge the needle cover to move to a second position partially beyond a distal tip of the needle shaft and oriented at an angle relative to a longitudinal axis of the needle shaft preventing the needle shaft from re-emerging from the needle cover, wherein the helical spiral coil spring is biased to axially and rotationally urge the second latch member into engagement with the first latch member to retain the needle cover in the first retracted position, wherein the needle cover is moveable proximally in an axial direction from the first retracted position to passively disengage the second latch member from the first latch member due to a proximal force exerted on the needle cover from contact with a patient's tissue during insertion of the Luer needle into the patient's tissue and upon proximal movement of the needle cover from the first retracted position, the spring being biased to rotationally urge the second latch member away from the first latch member to avoid reengagement of the first and second latch members upon distal movement of the needle cover as the Luer needle is withdrawn from the patient.

2. The safety device of claim 1 wherein the needle cover has a distal surface that is inwardly chamfered in the proximal direction and a distal hole in the center of the distal surface.

3. The safety device of claim 2 wherein the needle cover further comprises a locking hole aligned axially with the distal hole.

4. The safety device of claim 3 wherein needle shaft is misaligned with the distal hole in the distal surface when the needle cover is oriented in the second position partially beyond the distal tip of the needle shaft.

5. The safety device of claim 3 wherein the edges of the locking hole bite into the shaft of the needle to prevent movement of the needle cover relative to the needle shaft when the needle cover is oriented at an angle relative to the longitudinal axis of the needle shaft.

6. The safety device of claim 1 wherein the first latch member includes a recess engaged by the second latch member when the needle cover is retained in the first retracted position.

7. The safety device of claim 1 wherein the needle cover is integrally formed with the spring.

8. The safety device of claim 1 wherein the spring includes one or more mounting holes formed in the proximal coils of the spring.

9. The safety device of claim 7 wherein the Luer needle includes one or more mounting posts to couple the spring to the Luer needle.

10. A method for performing an injection using a passive anti-needle stick safety device including a Luer needle, a helical spiral coil spring coupled at a proximal end to the Luer needle and a needle tip cover coupled to the helical spiral coil spring at a distal end, the needle tip cover retained by cooperating latches on the Luer needle and the needle tip cover in a first retracted position wherein the needle is exposed beyond the needle tip cover, the helical spiral coil spring being biased to axially and rotationally urge the cooperating latches into engagement to retain the needle tip cover in a first retracted position and upon disengagement of the cooperating latches, urge a first cooperating latch away from a second cooperating latch and the needle tip cover towards a second extended position for covering and preventing the needle from reemerging from the needle tip cover, the method comprising:
inserting the needle into a patient's tissue a predetermined distance thereby exerting a proximal force on the needle tip cover from the patient's tissue causing the needle tip cover and a first cooperating latch on the needle tip cover to move axially in the proximal direction relative to a second cooperating latch on the Luer needle to passively disengage the first and second cooperating latches and, upon disengagement of the first and second cooperating latches, the helical spiral coil spring causing the needle tip cover to rotate about the Luer needle and rotate the first cooperating latch relative to the second cooperating latch to avoid reengagement of the first and second cooperating latches as the needle tip cover moves distally upon withdrawal of the Luer needle from the patient's tissue; and after the medication is injected into the patient, withdrawing the needle from the tissue thereby allowing the spring to extend to cover the needle and urge the needle tip cover to the second extended position wherein the needle is prevented from reemerging from the needle tip cover.

11. The method of claim 10, wherein the needle is withdrawn from the patient as the needle tip cover is extended partially beyond the tip of the needle and oriented at an angle relative to the longitudinal axis of the needle shaft.

12. The method of claim 11, wherein the needle shaft is misaligned with a distal hole in the needle tip cover preventing the needle shaft from reemerging from the needle tip cover.

13. The method of claim 11, wherein the needle shaft is misaligned with a locking hole preventing relative movement between the needle tip cover and the needle shaft.

14. The method of claim 10, wherein the first cooperating latch on the needle tip cover exerting a distal force and a rotational force on the second cooperating latch extending from the Luer needle when the needle tip cover is held in the first retracted position.

15. A safety device for use with a syringe having a needle comprising
a helical spiral coil spring couplable at a proximal end to the needle of the syringe, and
a needle tip cover coupled to the helical spiral coil spring at a distal end and slidably receivable over the needle shaft, the needle tip cover being lockable in a first retracted position along the needle shaft, wherein when the needle cover is retained in the first retracted position the helical spiral coil spring is biased to urge the needle cover to move to a second position partially beyond a distal tip of the needle shaft and oriented at an angle relative to a longitudinal axis of the needle shaft preventing the needle shaft from re-emerging from the needle cover, wherein the helical spiral coil spring is biased to axially and rotationally urge a first latch member on the needle tip cover into engagement with a second latch member to retain the needle cover in the first retracted position, wherein the needle cover is moveable proximally in an axial direction from the first retracted position to passively disengage the first latch member from the second latch member due to a proximal force exerted on the needle cover from contact with a patient's tissue during insertion of the needle into the patient's tissue and upon proximal movement of the needle cover from the first retracted position, the spring being biased to rotationally urge the first latch member away from the second latch member to avoid reengagement of the first and second latch members upon distal movement of the needle cover as the needle is withdrawn from the patient.

16. The safety device of claim 15 wherein the needle cover has a distal surface that is inwardly chamfered in the proximal direction and a distal hole in the center of the distal surface.

17. The safety device of claim 16 wherein the needle cover further comprises a locking hole aligned axially with the distal hole.

18. The safety device of claim 17 wherein needle shaft is misaligned with the distal hole in the distal surface when the needle cover is oriented in the second position partially beyond the distal tip of the needle shaft.

19. The safety device of claim 17 wherein the edges of the locking hole bite into the shaft of the needle to prevent movement of the needle tip cover relative to the needle shaft when the needle tip cover is oriented at an angle relative to the longitudinal axis of the needle shaft.

20. The safety device of claim 15 wherein a proximal end of the spring includes a proximal coil bent inwardly at an angle relative to the normal angle to the longitudinal axis of the needle, wherein the inwardly bent proximal coil includes a proximal locking hole slidably received over the needle.

21. The safety device of 15 wherein the needle tip cover is integral with the distal end of the spring as a single piece device.

22. The safety device of 15 wherein the helical spiral coil spring includes a first bent distal coil with a first distal locking hole, the first bent distal coil being bent inwardly in a first direction, and a second bent distal coil with a second distal locking hole, the second bent distal coil being bent inwardly in a second direction from the first bent distal coil, and wherein the needle tip cover extends from the second bent distal coil.

23. The safety device of claim 15 wherein the second latch member includes a recess engaged by the first latch member when the needle cover is retained in the first retracted position.

24. The safety device of claim 14 wherein the second latch member includes a recess engaged by the first latch member when the needle cover is retained in the first retracted position.

* * * * *